United States Patent [19]

Geller

[11] Patent Number: 4,693,871

[45] Date of Patent: Sep. 15, 1987

[54] DISPOSABLE ASEPTIC SHEATH FOR DENTAL HANDPIECES

[76] Inventor: Paul Geller, 4 Holland Ave., Elmont, N.Y. 11003

[21] Appl. No.: 849,808

[22] Filed: Apr. 9, 1986

[51] Int. Cl.$^4$ ............................................... A61C 1/16
[52] U.S. Cl. .................................................... 433/116
[58] Field of Search ........................................ 433/116

[56] References Cited

U.S. PATENT DOCUMENTS

| 949,273 | 2/1910 | Hinrichsen | 433/116 |
| 2,041,077 | 5/1936 | Lininger | 433/116 |
| 4,266,935 | 5/1981 | Hoppe | 433/116 |

FOREIGN PATENT DOCUMENTS 2029232  3/1980  United Kingdom ................ 433/116

Primary Examiner—Robert Peshock
Attorney, Agent, or Firm—Steinberg & Raskin

[57] ABSTRACT

An aseptic sheath for dental handpieces by the use of which the handpieces are eliminated as a possible source of transmission of microbial diseases. The sheath is formed of suitable resilient thermoplastic sheet material, preferably by vacuum forming, in a shape which corresponds to that of the particular handpiece with which it is to be used, e.g., to provide communicating spaces for substantially completely enclosing the head, neck and handle of a contra-angle handpiece. In use, the handpiece is inserted into the sheath by spreading normally overlapping edges of the sheath which extend longitudinally over at least the length of the handle-receiving portion to provide access for the handpiece to the sheath interior. After insertion is completed, the edges are released to snap back over the handpiece due to the resiliency of the sheath-forming material to substantially completely enclose the handpiece therewithin. After use, the handpiece is removed from the possibly contaminated sheath which is then discarded. The handpiece is ready for subsequent use in a new sheath. It is not necessary to disinfect the handpiece, such as by autoclaving, which has been found to affect the performance of the handpiece.

6 Claims, 10 Drawing Figures

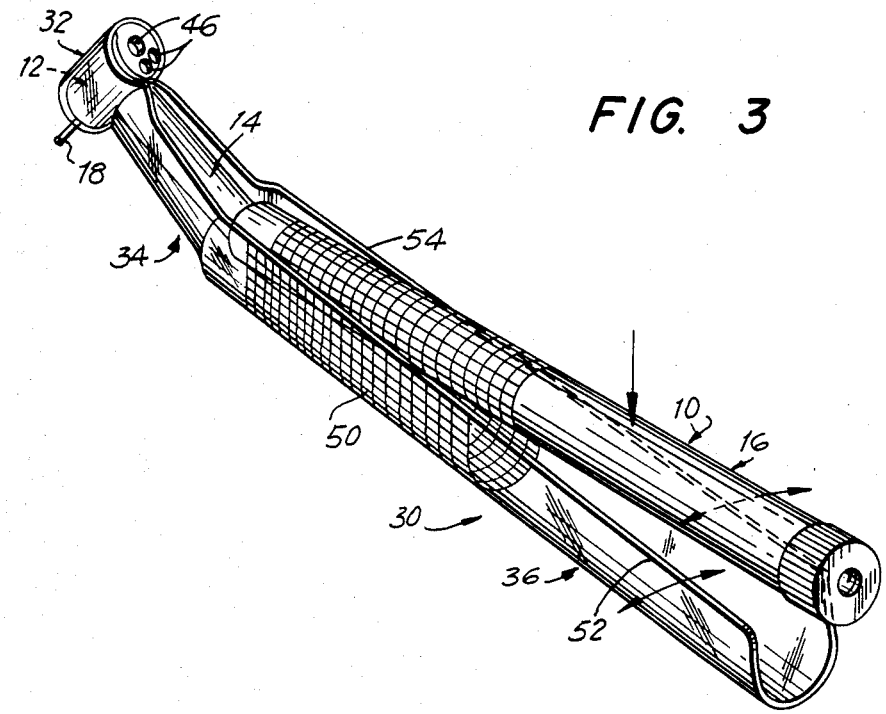
FIG. 3
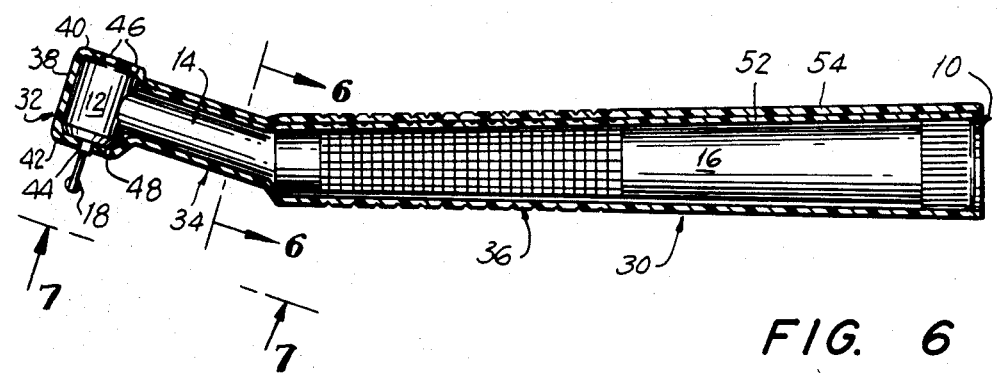
FIG. 5
FIG. 6
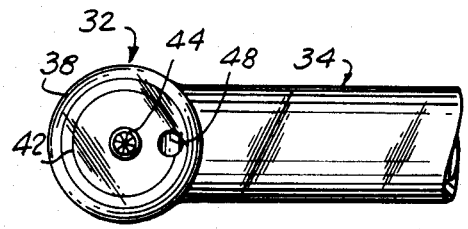
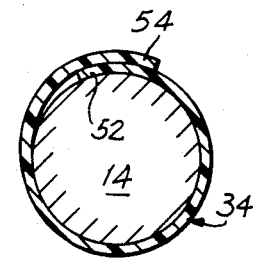
FIG. 7

DISPOSABLE ASEPTIC SHEATH FOR DENTAL HANDPIECES

BACKGROUND OF THE INVENTION

This invention relates generally to dentistry and, more particularly, to methods and apparatus for eliminating dental handpieces as a possible source of transmission of disease.

A significant concern exists that the dental operatory is a possible source of transmission of microbial disease, such as hepatitis B (serum hepatitis) and AIDS (acquired immune deficiency syndrome). Thus, it is thought that saliva may be a main vehicle for the transmission of such diseases and studies have shown that whereas the incidence of hepatitis B in the general population is 0.3%, up to 5% of the dental community has contracted a clinical infection. For this reason, sterilization and cleaning of dental instruments following each use is important to prevent microbial transmission to both dentists as well as to patients. Sterilization of dental instruments may be accomplished by any procedure that destroys a viral coat, including, for example, placement in 100° C. water for about thirty minutes or autoclaving in 121° C. steam at 15 psi for thirty minutes. The sterilization of dental hand instruments, such as probes, excavators, mouth mirrors, and forceps, has become routine.

The high-speed air-driven dental handpiece is a widely used dental instrument which is known to collect particulate matter and bacteria and may be a source of hepatitis or AIDS virus transmission. It has been conventional to disinfect high-speed handpieces by scrubbing with a detergent and wiping with alcohol after use. However, wiping may not remove all debris and short contact with disinfectant may not be sufficient for sterilization.

It has therefore been suggested that handpieces be designed so as to be autoclavable and that the handpiece should be sterilized by autoclaving after every use. However, studies have shown that this technique has drawbacks. For example, firstly, if autoclaving were to be routinely performed, several handpieces would be required for each operatory to account for turnaround time and malfunctions. Additional time for relubrication would also be required. For this reason, dentists may tend not to autoclave the handpieces. Secondly, autoclaving may not be effective in killing all microbes on and in the handpieces. Dried saliva and serum may protect organisms in the deep recesses of the handpiece. Lubrication oil covering the narrow internal parts of the handpieces shield spores from pressurized steam and acts as a protective flux. Studies have shown that the usual autoclaving schedules for downward displacement sterilizers with fixed programs, commonly used in the dentist's office, are not sufficiently effective to give a probability of $10^{-6}$ or less of surviving microorganisms being present. Thirdly, some dental handpieces can be damaged by conventional sterilization procedures which can undermine the efficiency of rubber gaskets. Fourthly, studies have shown that performance of handpieces which are sterilized by autoclaving deteriorates over a period of time. Thus, the speed of the handpiece decreases over a period of time when subjected to periodic autoclaving. The water spray from autoclaved handpieces becomes course. Resistance in the chuck to inserting and removing burs increases.

In summary, the high speed handpiece is a weak link in the chain of disinfection or sterilization in the dental office. At the present time there is no standardized effective means for sterilizing a conventional high speed handpiece for routine use.

SUMMARY OF THE INVENTION

It is a main object of the present invention to eliminate the dental handpiece as a possible source of transmission of disease.

Another object of the present invention is to provide a new and improved aseptic sheath for enclosing a dental handpiece during use which is intended to be disposed of or discarded after the dental procedure is completed to avoid contamination of the handpiece and transmission of disease through the handpiece.

Still another object of the present invention is to provide a new and improved disposable sheath for dental handpieces which effectively protects the handpiece from contamination during use while permitting the handpiece to be held and operated by the dentist in the conventional manner.

A further object of the present invention is to provide a new and improved disposable sheath for dental handpieces into which a handpiece can be inserted and from which a handpiece can be removed in a simple and quick manner and which is economical in manufacture.

Briefly, in accordance with the present invention, these and other objects are attained by providing an aseptic sheath formed of resilient thermoplastic sheet material, preferably by vacuum forming, in a shape which corresponds to that of the particular handpiece with which it is to be used, e.g., to provide communicating spaces for substantially completely enclosing the head, neck and handle of a contraangle handpiece. In use, the handpiece is inserted into the sheath by spreading normally overlapping edges of the sheath which extend longitudinally over at least the length of the handle portion of the sheath to provide access for the handpiece to the sheath interior. After insertion is completed, the edges are released to snap back over the handpiece due to the resiliency of the sheath-forming plastic sheet material to substantially completely enclose the handpiece therewithin. After use, the handpiece is removed from the possibly contaminated sheath which is then discarded. The handpiece is now ready for subsequent use in a new sheath.

The head portion of the aseptic sheath may be formed with openings for providing access to the handpiece for a tool for changing the handpiece bur, for providing passages through which air and water sprays may be discharged from the handpiece, and for providing a passage through which a bur passes.

DETAILED DESCRIPTION OF THE DRAWINGS

A more complete appreciation of the present invention and many of the attendant advantages thereof will be readily understood by reference to the following detailed description when considered in connection with the accompanying drawings in which:

FIG. 3 is a perspective view illustrating the insertion of a dental handpiece into an aseptic sheath in accordance with the present invention;

FIG. 5 is a partial sectional view taken along line 5—5 of FIG. 4;

FIG. 6 is a partial sectional view taken along line 6—6 of FIG. 5;

FIG. 7 is a view in the direction of line 7—7 of FIG. 5 illustrating the head and neck portions of the aseptic sheath with the handpiece inserted therewithin;

DESCRIPTION OF THE PREFERRED EMBODIMENTS

Figure 1:
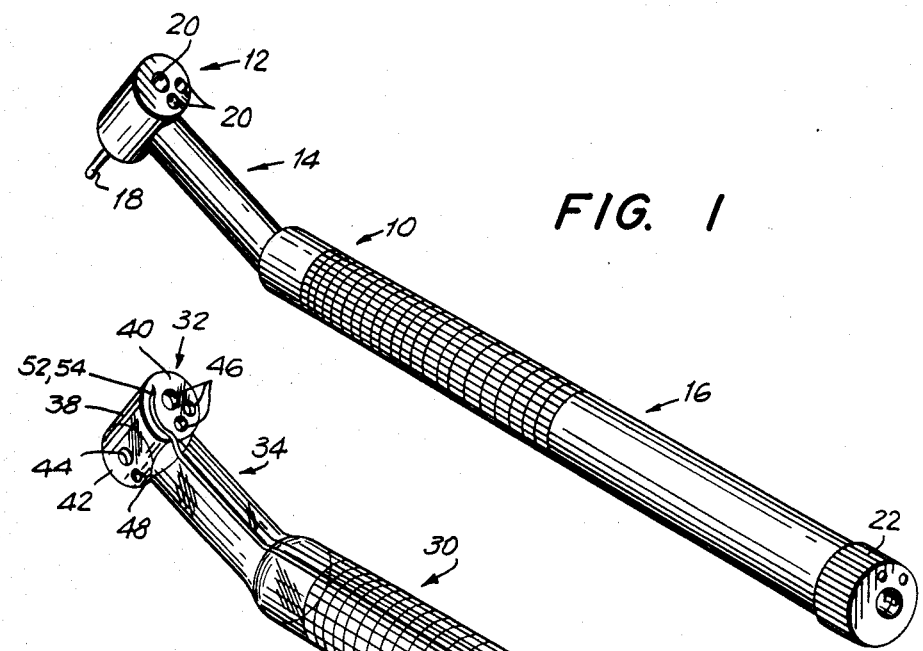
FIG. 1 is a perspective view of a conventional dental handpiece with which an aseptic sheath in accordance with the invention can be used.
Figure 2:
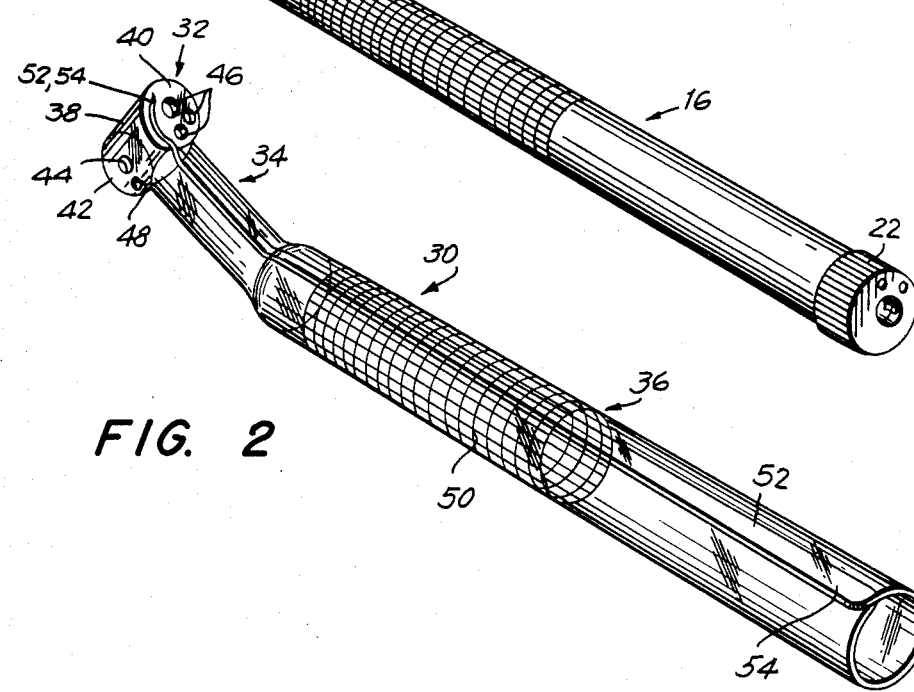
FIG. 2 is a perspective view of one embodiment of an aseptic sheath in accordance with the invention for use with the handpiece shown in FIG. 1.

Referring now to the drawings wherein like reference characters designate identical or corresponding parts throughout the several views, a conventional high-speed air-driven dental handpiece, generally designated 10, with which an aseptic sheath in accordance with the invention is used is shown in FIG. 1. The handpiece 10 includes a head 12 connected to one end of a neck 14 and a handle 16 connected to the other end of neck 14. An air turbine (not shown) is housed within head 12 to which an interchangeable bur 18 is coupled. Socket openings 20 of a bur chucking mechanism are accessible at the top of the head 12 for receiving a tool for changing the bur. A spray nozzle (not shown) is located adjacent to the bur through which a water spray is discharged from head 12 of handpiece 10. The neck 14 forms a contra-angle with handle 16 to facilitate maneuvering of the handpiece during use. The handle 16 and neck 14 house tubing through which pressurized air and water are conducted to the head 12 for driving the turbine and bur and for providing a water jet, respectively. A coupling 22 for the air and water supply is provided on the free end of handle 16. A handpiece of the type described above is available from Midwest American Company under the trademark Quiet-Air.

Handpieces of the type shown in FIG. 1 may be contaminated with saliva containing viral spores at several locations, including at the threaded connection of the neck and handle, within the bur opening in the head 12, and within the handle 16. Conventional sterilizing techniques have been found not to be totally effective and in fact have detracted from the performance of the handpiece as described above.

Referring now to FIGS. 2-7, one embodiment of the disposable sheath for preventing contamination of a dental handpiece in accordance with the present invention, generally designated 30 is illustrated. The sheath 30 is specifically adapted for use with a conventional dental handpiece of the type shown in FIG. 1 and described above.

Sheath 30 is formed of a single sheet of suitable resilient thermoplastic sheet material, preferably clear and transparent. Polyethylene sheet material having a thickness of 0.020 inches has been found satisfactory although it is understood that other materials and thicknesses may be utilized. For example, thermoplastic sheet material having thicknesses in the range of between about 0.002 inches to 0.060 inches would be satisfactory. Material thinner than that noted above would probably tear too easily while materials having thicknesses greater than those indicated above would lack the flexibility and resiliency necessary to the use of the sheath as described below.

The sheath 30 is formed, preferably by conventional vacuum forming techniques, to have a shape which closely corresponds to that of the handpiece. Thus, the sheath 30 which is intended for use with a handpiece of the type shown in FIG. 1, includes a head portion 32, a neck portion 34 and a handle portion 36 which define interior spaces which communicate with each other to substantially completely enclose the head, neck and handle 12, 14 and 16 of the handpiece 10, respectively.

The head portion 32 of the sheath 30 has a substantially cylindrical configuration defined by a side wall 38, a top wall 40 and a bottom wall 42. An opening 44 is formed through the bottom wall 42 through which the handpiece bur 18 passes when the handpiece is inserted within the sheath 30. Openings 46 are formed through the top wall 40 of head portion 32 which become aligned with the handpiece socket openings 20 upon insertion of the handpiece within the sheath thereby providing access for a tool for changing the handpiece bur 18. Similarly, an opening 48 is formed through the bottom wall 42 adjacent to bur opening 44 which becomes aligned with the water jet nozzle of the handpiece upon insertion of the handpiece within the sheath.

The neck portion 34 of sheath 30 has a substantially cylindrical configuration the axis of which extends substantially normal to the axis of the head portion 32. Handle portion 36 has an elongate substantially cylindrical configuration, the axis of which forms an angle somewhat less than 180° with the axis of neck portion 34 to provide a contra-angle bend which corresponds to that of the handpiece 16. Circumferential ridges 50 are preferably formed in the handle portion 36 to facilitate grasping of the sheath-handpiece assembly by the dentist during use.

Figure 4:
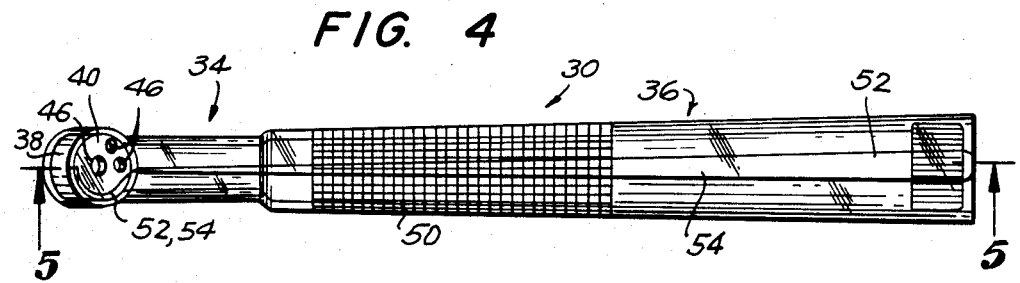
FIG. 4 is a top plan view of the assembly of the handpiece inserted within the aseptic sheath in accordance with the invention.

The sheath 30 is formed with free edge regions 52 and 54 which extend longitudinally over the entire lengths of the handle and neck portions 36 and 34 and which terminate at regions 52a, 54a which extend along the substantial periphery of the top wall 40 of head portion 32. In the normal unstressed condition of sheath 30, edge region 54 overlaps over edge region 52 (see FIG. 6) over their lengths which span the handle and neck portions 36 and 34. In the illustrated embodiment, the extent of overlap increases towards the rear or handle portion of the sheath 30 as best seen in FIG. 4. Due to the flexible and resilient nature of the material from which sheath 30 is formed, the edge regions 52 and 54 can be forceably spread apart and separated and, when released, the edge regions will snap back to assume the normal configuration described above.

In use, when it is desired to use the handpiece 10, the dentist inserts the handpiece into a fresh, sterile aseptic sheath 30 by forceably separating the overlapping edge regions 52 and 54 until the sheath has the configuration shown in FIG. 3. The head 12 of the handpiece is inserted into the head portion 32 of sheath 30 so that bur 18 extends through opening 44. This insertion is facilitated by the separable edge regions 52a and 54a formed in the top wall 40 of head portion 32. The neck 14 and then the handle 16 of the handpiece are then substantially laterally inserted through the space between the separated edge regions 52 and 54 into the neck and handle portions 34 and 36 of sheath 30 as seen in FIG. 3. When insertion has been completed, the edge regions 52 and 54 are released whereupon they snap back due to the resiliency of the material from which the sheath is formed to assume their overlapped positions. As seen in FIGS. 4 and 5, the handpiece 10 is substantially completely enclosed within sheath 30. Moreover, it is not possible for the handpiece 10 to move within sheath 30 due to the contra-angle bend and the fact that the axis of the cylindrical head portion 32 is substantially normal to the axis of the cylindrical neck portion 34. As noted above, the openings 46 in the top wall 40 of the sheath head portion 32 are aligned with the socket openings 20 of the handpiece so that when it is desired to change a bur 18, a tool can simply be inserted through openings 46 into socket openings 20. The opening 48 formed in the bottom wall 42 of sheath head portion 32 is aligned with the water discharge nozzle of the handpiece so that during operation, a water jet can be directed into the patient's mouth in the same manner as in the case where a dental handpiece is used without the sheath of the invention. Due to the overlapping positions of the edge regions 52 and 54, it is substantially impossible for the handpiece 10 to become contaminated by saliva or the like. During use, since the shape of the aseptic sheath 30 substantially corresponds to that of the handpiece 10, the dentist can retain the familiar operational techniques used previously. The ridges 50 provided on the handle portion 36 of sheath 30 facilitate the gripping of the sheath-handpiece assembly by the dentist. After the procedure has been completed, the handpiece 10 is withdrawn from sheath 30 by spreading the edge regions 52 and 54 apart (see FIG. 3) and effecting the insertion procedure in reverse. The handpiece remains in a substantially sterile condition without the need for additional sterilizing operations. When it is desired to again use the handpiece, it is only necessary to insert the handpiece into a new, uncontaminated aseptic sheath.

Figure 8:
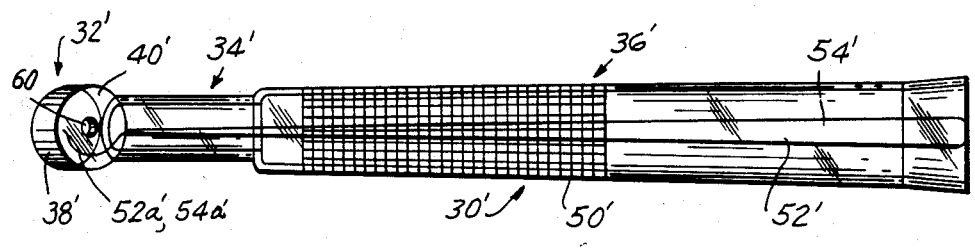
FIG. 8 is a top plan view of another embodiment of an aseptic sheath in accordance with the present invention.
Figure 9:
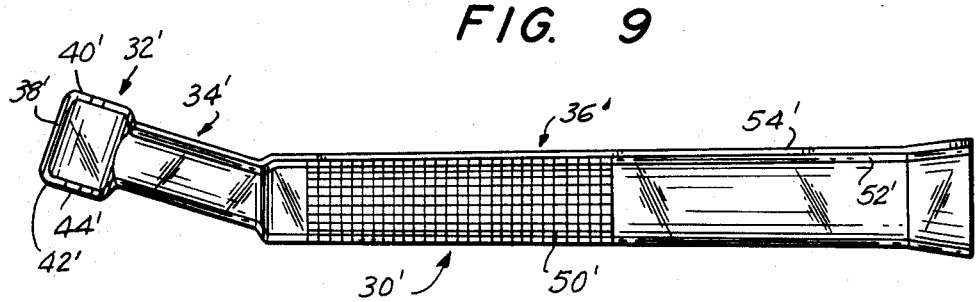
FIG. 9 is a side elevation view in partial section of the aseptic sheath of FIG. 8.
Figure 10:
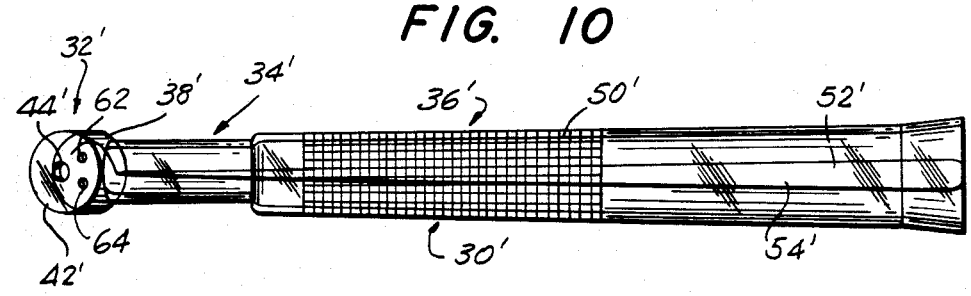
FIG. 10 is a bottom plan view of the aseptic sheath shown in FIG. 8.

Referring to FIGS. 8–10, a second embodiment of an aseptic sheath 30' in accordance with the invention is illustrated. Parts of the aseptic sheath 30' which correspond to those of the first embodiment described above are designated by the same reference numerals, prime. The aseptic sheath 30' is adapted for use with a conventional dental handpiece which is somewhat different from the handpiece 10. In particular, sheath 30' is adapted for use with a handpiece available from Star Dental Manufacturing Co., Inc. under the trademark Futura II. This handpiece essentially differs from handpiece 10 in that only a single socket opening is provided for changing the bur and in that two openings are provided adjacent to the bur opening for discharging both water and air jets. Accordingly, the sheath 30' differs from sheath 30 in that only a single socket opening 60 is formed in the top wall 40' of the head portion 32' and a pair of openings 62 and 64 are provided for the water jet spray to pass through. The sheath 30' is in all other essential respects substantially the same as sheath 30.

It is seen from the foregoing that an aseptic sheath is provided which substantially completely covers the handpiece during use to prevent the handpiece from becoming contaminated and act as a source of transmission of disease. The handpiece is constructed of inexpensive material so that it can be discarded after each dental procedure is completed. Since the shape of the sheath closely conforms to the shape of the handpiece, it is not necessary for the dentist to learn any new procedures. Rather, the sheath-handpiece assembly can be held and operated by the dentist in a conventional manner. The handpiece can be inserted into and removed from the sheath in a simple and quick manner and yet the handpiece is held reliably within the sheath without the possibility of movement therewithin.

Obviously, numerous modifications and variations of the present invention are possible in the light of the above teachings. It is therefore to be understood that within the scope of the claims appended hereto, the invention may be practiced otherwise than as specifically disclosed herein.

What is claimed is:

1. A disposable aseptic sheath for a dental handpiece having a head, neck and handle, said sheath adapted for substantially completely enclosing the handpiece therewithin during use to prevent the handpiece from becoming contaminated, comprising:

a forward substantially cylindrical and rigid head portion for receiving the head of the handpiece;

an intermediate substantially cylindrical and rigid neck portion integral with said head portion for receiving the neck of the handpiece, said neck portion having two ends and being joined to said head portion at one of said ends;

a rearward substantially cylindrical and rigid handle portion integral with said neck and head portions for receiving the handle of the handpiece, said handle portion being joined to the other of said ends of said neck portion;

said head, neck and handle portions being formed from a unitary, elastically deformable sheet of resilient thermoplastic material having a thickness in the range of between about 0.002 to 0.060 inches; and said sheath including a pair of edge regions extending substantially longitudinally over said neck and handle portions in normally mutual overlapping relationship over at least a portion of their lengths, said overlapping edge regions being forceably separable out of overlapping relationship to form a space between them extending longitudinally over said neck and handle portions providing access for substantially lateral insertion of the handpiece into the interior of said sheath, whereby upon insertion of the handpiece, said edge regions return into said mutual overlapping relationship due to the resilience of said sheet material of which said sheath is formed.

2. The combination of claim 1 wherein the axis of said head portion extends at a substantially right angle to the axis of said neck portion, and wherein said head portion includes a substantially cylindrical side wall and opposed top and bottom walls, an opening formed in said bottom wall through which a bur is adapted to pass and at least one opening formed in said top wall for providing access to the interior of said head portion for a bur-changing tool.

3. The combination of claim 2 wherein said neck and handle portions are substantially cylindrical and wherein the axes of said neck and handle portions form an angle with each other of less than 180°.

4. The combination of claim 1 wherein the extent to which said free edge regions overlap increases in the rearward direction.

5. The combination of claim 2 wherein at least one additional opening is formed in said bottom wall for passage of at least one of a water and air jet.

6. A disposable aseptic sheath for a dental handpiece having a head portion and elongate neck and handle portions, integrally joined to each other, for substantially completely enclosing the head, neck and handle of the handpiece, respectively, therewithin during use to prevent the handpiece from becoming contaminated, comprising:
- a single unitary, elastically deformable sheet of resilient thermoplastic sheet material formed to include a pair of edge regions extending substantially longitudinally over said neck and handle portions in normally mutual overlapping relationship over at least a portion of their lengths, said overlapping edge regions being forceably separable out of overlapping relationship to form a space between them extending longitudinally over said neck and handle portions providing access for substantially lateral insertion of the handpiece into the interior of said sheath,
- whereby upon insertion of the handpiece, said edge regions return into said mutual overlapping relationship due to the resilience of said sheet material of which said sheath is formed.

* * * * *